United States Patent
Desponds et al.

(10) Patent No.: US 7,230,111 B2
(45) Date of Patent: Jun. 12, 2007

(54) CATALYTIC PROCESS FOR THE PREPARATION OF THIAZOLE DERIVATIVES

(75) Inventors: Olivier Desponds, Monthey (CH); Dominik Faber, Schweizerhalle (CH); Rémy Gressly, Monthey (CH); Thomas Rapold, Münchwilen (CH); Marco Passafaro, Schaffhausen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 533 days.

(21) Appl. No.: 10/362,500

(22) PCT Filed: Aug. 21, 2001

(86) PCT No.: PCT/EP01/09663

§ 371 (c)(1),
(2), (4) Date: Jul. 11, 2003

(87) PCT Pub. No.: WO02/16335

PCT Pub. Date: Feb. 28, 2002

(65) Prior Publication Data

US 2004/0030148 A1    Feb. 12, 2004

(30) Foreign Application Priority Data

Aug. 23, 2000  (CH) ...................... 1651/00
Aug. 23, 2000  (CH) ...................... 1653/00

(51) Int. Cl.
*C07D 277/20*    (2006.01)

(52) U.S. Cl. ..................................... 548/202

(58) Field of Classification Search ................. 548/202
See application file for complete search history.

(56) References Cited

FOREIGN PATENT DOCUMENTS

| EP | 0260560 | 3/1988 |
|---|---|---|
| EP | 0446913 | 9/1991 |
| WO | 9832747 | 7/1998 |

*Primary Examiner*—Taofiq Solola
(74) *Attorney, Agent, or Firm*—Rebecca Gegick

(57) ABSTRACT

A process for the preparation of a compound of formula (I)

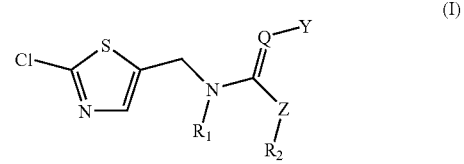

(I)

wherein Q is CH or N; Y is $NO_2$ or CN; Z is $CHR_3$, O, $NR_3$ or S; $R_1$ and $R_2$ are $C_1$-$C_8$ alkyl or together form an alkylene bridge having two or three carbon atoms; by reacting a compound of formula $H_2C=C(X)CH_2NCS$ wherein X is a leaving group, with a chlorinating agent in the presence of a catalytic amount of $SO_2$. to form a compound of formula (III)

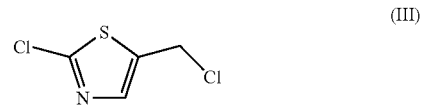

(III)

and the compound of formula (III) is reacted with a compound of formula $R_1NHC(=QY)ZR_2$ wherein $R_1$, $R_2$, Y, Z and Q are as defined for compound (I).

1 Claim, No Drawings

CATALYTIC PROCESS FOR THE PREPARATION OF THIAZOLE DERIVATIVES

This application is a 371 filing of International Application No. PCT/EP01/09663, filed Aug. 21, 2001, the contents of which are incorporated herein by reference.

The invention relates (A) to a process for the preparation of a compound of formula

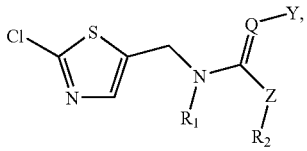

and, where appropriate, E/Z isomers, mixtures of E/Z isomers and/or tautomers thereof, in each case in free form or in salt form, wherein Q is CH or N;
Y is $NO_2$ or CN;
Z is $CHR_3$, O, $NR_3$ or S;
$R_1$ and $R_2$ either are each independently of the other hydrogen or $C_1$-$C_8$alkyl which is unsubstituted or substituted by $R_4$ or together are an alkylene bridge having two or three carbon atoms which optionally contains a hetero atom selected from the group consisting of $NR_5$, O and S,
$R_3$ is H or $C_1$-$C_{12}$alkyl which is unsubstituted or substituted by $R_4$,
$R_4$ is unsubstituted or substituted aryl or heteroaryl, and
$R_5$ is H or $C_1$-$C_{12}$alkyl; wherein a) a compound of formula

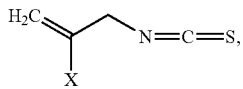

which is known or which can be prepared by known methods and wherein X is a leaving group, is reacted with a chlorinating agent to form a compound of formula

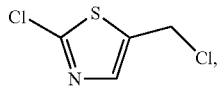

or, where appropriate, a tautomer thereof, in each case in free form or in salt form; and b) the compound of formula (III) thereby obtained is reacted with a compound of formula

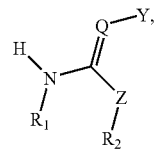

which is known or which can be prepared by methods known per se and wherein $R_1$, $R_2$, Y, Z and Q are as defined hereinbefore for the compound of formula (I);

in which process the chlorination according to process step a) is performed using a chlorinating agent in the presence of catalytic amounts of $SO_2$;

to a process for the preparation of a compound of formula (III) according to process step a) hereinbefore, and to the use of compounds of formulae (II), (III) and (IV) in a process as described hereinbefore.

The compounds of formula (I) are known as valuable pesticides, and synthesis methods for those compounds are described in the literature. It has, however, been found that significant safety problems occur in the case of those processes known from the literature. It has moreover been found that the compound of formula (III) prepared according to the known processes does not satisfy the requirements in terms of purity either, that it is—probably because of those impurities—thermally unstable, which in turn can lead to significant problems in a production plant, and also that the known processes have significant disadvantages in respect of further parameters, for example yield, duration of the synthesis cycle, volume yield, disposal of ecologically and toxicologically problematic wastes, for example solvents, $SO_2$, and the like.

The known preparation processes are therefore not satisfactory in every respect, which is why there is a need to provide improved preparation processes for the compounds of formula (I) and especially of formula (III).

In Example 1 of EP-A-446 913, the compound of formula (II) hereinbefore is reacted with chlorine, 2-chloro-5-chloromethyl-thiazole of formula (III) above being obtained in a crude yield of 73%. In Example 2 of EP-A-446 913, the same reaction is carried out, but using $SO_2Cl_2$ instead of chlorine. The crude yield in that Example is 82%. The content of 2-chloro-5-chloromethyl-thiazole is not mentioned in Example 1 of EP-A-446 913. In Example 2, a content of slightly more than 90% 2-chloro-5-chloromethyl-thiazole is mentioned, from which it is possible to deduce a yield of about 74% of theory. The increased yield in the case of the process using $SO_2Cl$, however, is itself a major advantage for production on a large industrial scale: using the method carried out with $SO_2Cl_2$, more material can be prepared in the same unit of time than when $Cl_2$ is employed, certain waste substances are produced in significantly smaller amounts by that means, and there are further advantages besides. However, the use of $SO_2Cl_2$ has the significant disadvantage that stoichiometric amounts of $SO_2$ are produced, which have to be removed, either by recycling the $SO_2$ to $SO_2Cl_2$ using $Cl_2$ or by having to convert the $SO_2$ into $SO_4^{2-}$ by oxidation. However, $SO_4^{2-}$ is a waste substance which, although not ecologically harmful, seriously attacks the concrete walls of waste water purification systems and is therefore extremely undesirable. The conversion of $SO_2$ to $SO_2Cl_2$ using $Cl_2$, on the other hand, naturally requires a specific production system to be set up. There is therefore a need to improve the reaction step from the compound of formula (II) to the compound of formula (III) so that the advantages of carrying out the process with $SO_2Cl_2$ can be exploited without being confronted with the mentioned problems of waste. According to the invention, it has been possible, surprisingly, to solve the problem by simple means.

In this respect, it is mentioned in EP-A-446 913, Example 1, that when the compound of formula

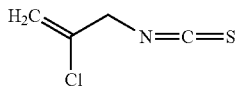

(IIa) is chlorinated in chloroform there is first formed a mixture of intermediates, the structures of which are postulated as being

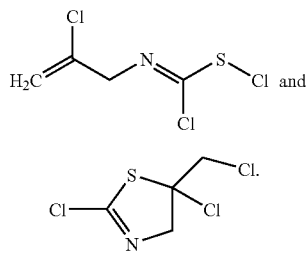

That mixture of intermediates is allowed to react completely, with cooling at about +40° C., to form the compound of formula (III). It has now been found that, in the case of that procedure, a dangerous heating potential, inter alia, is built up, which in an unfavourable case may result in a major incident. In a particular embodiment of the process according to the invention, that problem is avoided by carrying out the reaction continuously, only small amounts of the said intermediates being accumulated per unit of time and, moreover, the residence times in the individual reactors being short.

Some compounds of formulae (I) to (IV) contain asymmetric carbon atoms, as a result of which the compounds may occur in optically active forms. Formulae (I) to (IV) are intended to include all those possible isomeric forms, and mixtures thereof, for example racemates or mixtures of E/Z isomers.

The general terms used hereinbefore and hereinafter have the following meanings, unless defined otherwise:

Unless otherwise defined, carbon-containing groups and compounds each contain from 1 up to and including 8, preferably from 1 up to and including 6, especially from 1 up to and including 4, and more especially 1 or 2, carbon atoms.

Alkyl, both as a group per se and as a structural element of other groups and compounds, for example haloalkyl, arylalkyl and hydroxyalkyl, is, in each case taking due account of the particular number of carbon atoms contained in the group or compound in question, either straight-chained, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl, both as a group per se and as a structural element of other groups and compounds, for example haloalkenyl and arylalkenyl, is, in each case taking due account of the particular number of carbon atoms contained in the group or compound in question, either straight-chained, for example vinyl, 1-methylvinyl, allyl, 1-butenyl or 2-hexenyl, or branched, for example isopropenyl.

Alkynyl, both as a group per se and as a structural element of other groups and compounds, for example haloalkynyl, is, in each case taking due account of the particular number of carbon atoms contained in the group or compound in question, either straight-chained, for example propargyl, 2-butynyl or 5-hexynyl, or branched, for example 2-ethynylpropyl or 2-propargylisopropyl.

$C_3$-$C_6$Cycloalkyl is cyclopropyl, cyclobutyl, cyclopentyl or cyclohexyl, especially cyclohexyl.

Aryl is phenyl or naphthyl, especially phenyl.

Heteroaryl is to be understood as being a five- to seven-membered monocyclic aromatic ring having from one to three hetero atoms selected from the group consisting of N, O and S, especially N and S, or a bicyclic heteroaryl that may contain either in only one ring —as, for example, in quinolinyl, quinoxalinyl, indolinyl, benzothiophenyl or benzofuranyl—or in both rings—as, for example, in pteridinyl or purinyl—independently of one another one or more hetero atoms selected from N, O and S. Preference is given to pyridyl, pyrimidinyl, thiazolyl and benzothiazolyl.

Halogen, both as a group per se and as a structural element of other groups and compounds, for example haloalkyl, haloalkenyl and haloalkynyl, is fluorine, chlorine, bromine or iodine, especially fluorine, chlorine or bromine, more especially chlorine or bromine, and very especially chlorine.

Halo-substituted, carbon-containing groups and compounds, for example haloalkyl and haloalkenyl, may be partially halogenated or perhalogenated, the halogen substituents in the case of multiple halogenation being identical or different. Examples of haloalkyl, both as a group per se and as a structural element of other groups and compounds, for example haloalkenyl, are methyl mono- to tri-substituted by fluorine, chlorine and/or by bromine, for example $CHF_2$ or $CF_3$; ethyl mono- to penta-substituted by fluorine, chlorine and/or by bromine, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl each mono- to hepta-substituted by fluorine, chlorine and/or by bromine, for example $CH_2CHBrCH_2Br$, $CF_2CHFCF_3$, $CH_2CF_2CF_3$ or $CH(CF_3)_2$; and butyl, or one of the isomers thereof, mono- to nona-substituted by fluorine, chlorine and/or by bromine, for example $CF(CF_3)CHFCF_3$ or $CH_2(CF_2)_2CF_3$. Haloalkenyl is, for example, $CH_2CH=CHCl$, $CH_2CH=CCl_2$, $CH_2CF=CF_2$ or $CH_2CH=CHCH_2Br$.

A leaving group X is to be understood hereinbefore and hereinafter as being any removable group customarily considered for chemical reactions, as will be known to the person skilled in the art, especially a halogen such as fluorine, chlorine, bromine or iodine, —O—C(=O)—A, —O—P(=O)(—A)$_2$, —O—Si($C_1$-$C_8$alkyl)$_3$, —O—($C_1$-$C_8$alkyl), —O-aryl, —O—S(=O)$_2$A, —S—P(=O)(—A)$_2$, —S—P(=S)(—A)$_2$, —S—($C_1$-$C_8$alkyl), —S-aryl, —S(=O)A, —S(=O)$_2$A or —O—C(=)—A wherein A is unsubstituted or substituted $C_1$-$C_8$alkyl, $C_2$-$C_8$alkenyl or $C_2$-$C_8$alkynyl, unsubstituted or substituted aryl, unsubstituted or substituted benzyl, $C_1$-$C_8$alkoxy or di($C_1$-$C_8$alkyl) amine wherein the alkyl groups are independent of one another; $NO_3$, $NO_2$, or sulfate, sulfite, phosphate, phosphite, carboxylate, imino ester, $N_2$ or carbamate.

Some compounds of formulae (I) to (IV) may be in the form of tautomers. Those compounds are therefore to be understood hereinbefore and hereinafter as including corresponding tautomers, even if the latter are not specifically mentioned in each case.

Compounds of formulae (I) to (IV) having at least one basic centre are capable, for example, of forming acid addition salts. Those acid addition salts are formed, for example, with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted or substituted, e.g. halo-substituted, $C_1$-$C_4$alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Furthermore, compounds of formulae (I) to (IV) having at least one acid group are capable of forming salts with bases. Suitable salts with bases are, for example, metal salts, such as alkali metal and alkaline earth metal salts, e.g. sodium, potassium and magnesium salts, and salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally also be formed. The compounds of formulae (I) to (IV) are to be understood hereinbefore and hereinafter as including both the compounds of formulae (I) to (IV) in free form and the corresponding salts. The same is correspondingly true for tautomers of compounds of formulae (I) to (IV) and salts thereof. In the case of the compounds of formulae (I) and (III), preference is generally given in each case to a process for the preparation of the free form.

Preference is given within the scope of the invention to a process for the preparation of a compound of formula (I)

(1) wherein $R_1$ and $R_2$ in the compounds of formulae (I) and (IV) either are each independently of the other hydrogen or $C_1$-$C_4$alkyl or together are a two- or three-membered alkylene bridge which optionally contains a hetero atom from the group consisting of $NR_5$, O and S, and $R_5$ is H or $C_1$-$C_4$alkyl;

and especially are hydrogen or together are a two- or three-membered alkylene bridge which optionally contains a hetero atom from the group consisting of $NR_5$ and O, and $R_5$ is $C_1$-$C_4$alkyl;

and more especially $R_1$ and $R_2$ together are —$CH_2$—O—$CH_2$—, —$CH_2$—$CH_2$—$CH_2$— or —$CH_2$—$CH_2$—;

(2) wherein Q is N;

(3) wherein Y is $NO_2$;

(4) wherein Z is $NR_3$ and $R_3$ is H or $C_1$-$C_4$alkyl;

(5) wherein, in process step a), the reaction temperature is in the range from −30° C. to 100° C., preferably from 0° C. to 50° C., especially from 20° C. to 45° C.;

(6) wherein the reaction according to process step a) is carried out in acetonitrile in a temperature range from 0° C. to 30° C., preferably at 20° C.;

(7) wherein X in the compound of formula (II) is halogen such as fluorine, chlorine, bromine or iodine, —O—C(=O)—A, —O—P(=O)(—A)$_2$, —O—S(=O)$_2$A, —S—P(=O)(—A)$_2$, —S—P(=S)(—A)$_2$, —S(=O)A or —S(=O)$_2$A, wherein A is unsubstituted or substituted $C_1$-$C_8$alkyl, $C_2$-$C_8$alkenyl or $C_2$-$C_8$alkynyl, unsubstituted or substituted aryl, unsubstituted or substituted benzyl, $C_1$-$C_8$alkoxy or di($C_1$-$C_8$alkyl)amine wherein the alkyl groups are independent of one another; especially wherein X is chlorine, bromine or iodine, more especially chlorine or bromine; very especially wherein X is chlorine;

(8) wherein $SO_2$ is used in an amount of from 1 mol % to 50 mol %, preferably from 10 mol % to 40 mol %, especially from 15 mol % to 30 mol %, based on the starting material of formula (II);

(9) wherein $SO_2$ is used in the form of $SO_2$ gas or in the form of an $SO_2$-releasing agent, preferably $SO_2Cl_2$;

(10) wherein in process step a) a continuous procedure is employed.

Especially suitable process conditions can be found in the Examples.

The process is especially suitable for the preparation of thiamethoxam, known from WO 98/32747; and of Ti-435 (clothianidin), known from EP-A-446 913.

Process Step a):

The reaction of process step a) described hereinbefore and hereinafter is carried out, if necessary, in a closed vessel, under pressure, in an inert gas atmosphere and/or under anhydrous conditions. Especially advantageous reaction conditions can be found in the Examples.

The reactants can be reacted with one another as such, i.e. without a solvent or diluent, for example in molten form. In most cases, however, the addition of a solvent or diluent is advantageous. Suitable solvents include aprotic solvents, especially, for example: aliphatic, aromatic and alicyclic hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, carbon tetrachloride, dichloroethane, trichloroethene and tetrachloroethene; esters, such as ethyl acetate, methyl acetate, dimethyl carbonate, diethyl carbonate, methyl formate, ethyl formate, ethoxyethyl acetate and methoxyethyl acetate; ethers, such as diethyl ether, dipropyl ether, diisopropyl ether, dibutyl ether, tert-butyl methyl ether, ethylene glycol dimethyl ether, dimethoxydiethyl ether, tetrahydrofuran and dioxane; ketones, such as acetone, methyl ethyl ketone, methyl isopropyl ketone and methyl isobutyl ketone; amides, such as N,N-dimethylformamide, N,N-diethylformamide, N,N-dimethylacetamide, N-methylpyrrolidone and hexamethylphosphoric acid triamide; nitriles, such as acetonitrile and propionitrile; and sulfoxides, such as dimethyl sulfoxide; nitroalkanes and aromatic nitro compounds, such as nitromethane, nitroethane and nitrobenzene; or mixtures of such solvents. Preference is given to polar aprotic solvents, especially carboxylic acid derivatives such as amides and nitriles; especially preferred solvents can be found in the Examples.

Suitable chlorinating agents include especially chlorine, $POCl_3$, $PCl_3$, $PCl_5$ and $SO_2Cl_2$; more especially chlorine or $SO_2Cl_2$, very especially a mixture of chlorine and $SO_2Cl_2$.

Catalytic amounts are to be understood as less-than-stoichiometric amounts based on the starting material of formula (II). $SO_2$ may either be added as such in gaseous form, or a compound capable of releasing $SO_2$ may be added. $SO_2Cl_2$ is especially suitable for that purpose.

In a preferred variant of process step a), some or all of the $SO_2Cl_2$ required for the catalysis is first metered in and only then is the chlorinating agent, preferably $Cl_2$, added.

Process Step b):

The reactants can be reacted with one another as such, i.e. without the addition of a solvent or diluent, for example in molten form. In most cases, however, the addition of an inert solvent or diluent, or a mixture thereof, is advantageous. Examples of such solvents or diluents that may be mentioned are more or less the same as those mentioned under process step a), although in addition protic solvents, such as alcohols and protic amides, are also suitable. When the reaction in question is carried out in the presence of a base, bases used in excess, such as triethylamine, pyridine, N-methylmorpholine or N,N-diethylaniline, may also serve as solvents or diluents.

The reaction is carried out preferably at a temperature of from approximately 0° C. to approximately +180° C., especially from about +10° C. to about +80° C., in many cases between room temperature and the reflux temperature of the solvent. In an especially preferred embodiment of process step b), a compound of formula (IV) is reacted at from 0° C. to 120° C., especially from 20° C. to 80° C., preferably from 30° C. to 60° C., in an ester, especially in dimethyl carbonate, and preferably in the presence of a base, especially $K_2CO_3$.

The reaction is preferably carried out at normal pressure.

The reaction time is not critical; preference is given to a reaction time of from 0.1 to 48 hours, especially from 0.5 to 12 hours.

The product is isolated by the usual methods, for example by filtration, crystallisation, distillation or chromatography or any suitable combination of such methods.

The yields achieved are usually good. It is often possible to obtain a yield of 80% of the theoretical value.

Preferred conditions under which the reaction is carried out can be found in the Examples.

Salts of compounds of formulae (I) to (IV) can be prepared in a manner known per se. For example, acid addition salts are obtained by treatment with a suitable acid or a suitable ion exchange reagent and salts with bases by treatment with a suitable base or a suitable ion exchange reagent.

Salts of compounds of formulae (I) to (IV) can be converted into the free compounds of formulae (I) to (IV) in customary manner; acid addition salts can be converted, for example, by treatment with a suitable basic medium or a suitable ion exchange reagent and salts with bases, for example, by treatment with a suitable acid or a suitable ion exchange reagent.

Salts of compounds of formulae (I) to (IV) can be converted into different salts of compounds of formulae (I) to (IV) in a manner known per se; for example, acid addition salts can be converted into different acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt being formed, for example silver chloride, is insoluble and is therefore precipitated out from the reaction mixture.

Depending upon the procedure and/or the reaction conditions, the compounds of formulae (I) to (IV) having salt-forming properties can be obtained in free form or in the form of salts.

The compounds of formulae (I) to (IV) and, in each case, where applicable, the tautomers thereof, in each case in free form or in salt form, may be in the form of one of the possible isomers or in the form of a mixture thereof, for example depending upon the number of asymmetric carbon atoms occurring in the molecule and the absolute and relative configuration thereof and/or depending upon the configuration of non-aromatic double bonds occurring in the molecule, in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood accordingly hereinbefore and hereinafter, even when stereochemical details are not specifically mentioned in each case.

Mixtures of diastereoisomers or mixtures of racemates of compounds of formulae (I) to (IV), or salts thereof, obtainable in accordance with the process—depending upon the starting materials and procedures chosen—or by other means can be separated into the pure diastereoisomers or racemates in known manner on the basis of the physicochemical differences between the constituents, for example by fractional crystallisation, distillation and/or chromatography.

Mixtures of enantiomers, such as racemates, so obtainable can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, via the formation of inclusion compounds, for example using chiral crown ethers, in which case only one enantiomer is complexed, or by conversion into diastereoisomeric salts, for example by reacting a basic end product racemate with an optically active acid, such as a carboxylic acid, for example camphoric acid, tartaric acid or malic acid, or a sulfonic acid, for example camphorsulfonic acid, and separating the mixture of diastereoisomers obtainable in that manner, for example on the basis of their different solubilities by fractional crystallisation, into the diastereoisomers, from which the desired enantiomer can be freed by the action of suitable, for example basic, media.

Pure diastereoisomers and enantiomers can be obtained not only by separation of corresponding mixtures of isomers but also, according to the invention, by generally known methods of diastereoselective or enantioselective synthesis, for example by carrying out the process according to the invention with starting materials that have appropriate stereochemistry.

The compounds of formulae (I) to (IV), and salts thereof, may also be obtained in the form of hydrates and/or may include other solvents, for example solvents that may optionally have been used for the crystallisation of compounds that occur in solid form.

The invention relates to all those embodiments of the process according to which a compound obtainable as starting material or intermediate at any stage of the process is used as starting material and all or some of the remaining steps are carried out, or in which a starting material is used in the form of a derivative or a salt and/or its racemates or antipodes, or, especially, is formed under the reaction conditions.

Compounds of formulae (I), (III) and (IV) obtainable in accordance with the process or by other means can be converted into different corresponding compounds in a manner known per se.

In the processes of the present invention there are preferably used those starting materials and intermediates, in each case in free form or in salt form, which result in the compounds of formula (I) or salts thereof described at the beginning as being especially valuable.

The invention relates especially to the preparation processes described in the Examples.

The present invention relates also to the process for the preparation of a compound of formula (III) from a compound of formula (II) according to process step a) as defined hereinbefore.

The preferences applying to the substituents of compounds of formula (IV) are the same as those mentioned hereinbefore in the processes for the preparation of compounds of formula (I).

The compounds of formulae (II) and (IV) are known, for example as intermediates for the preparation of pesticides, or they can be prepared using processes known per se.

PREPARATION EXAMPLES

A) Preparation of 2-chloro-5-chloromethyl-thiazole

Example P1

10 g of SO$_2$ are introduced at 20° C. into a solution of 73 g of 2-chloro-3-isothiocyanato-1-propene in 133 g of chlorobenzene. Then, over the course of 6 hours, 45 g of chlorine are introduced under the surface. The reaction mixture is then heated to 50° C., which is maintained until the evolution of gas ceases. There are obtained 232 g of a solution which, according to gas chromatographic analysis, contains 29.4% 2-chloro-5-chloromethylthiazole by weight. Yield: 81.3% of theory, based on 2-chloro-3-isothiocyanato-1-propene.

Example P2

In an analogous experiment, 49 g of chlorine are used without the catalyst, the other amounts of chemicals used and the reaction parameters being left the same as in Example 1. There are obtained 236 g of a solution which, according to gas chromatographic analysis, contains 20.9% 2-chloro-5-chloromethyl-thiazole by weight. Yield: 58.5% of theory, based on 2-chloro-3-isothiocyanato-1-propene.

Example P3

35 g of SO$_2$ are introduced, at 30° C., into a solution of 509 g of 2-chloro-3-isothiocyanato-1-propene in 931 g of chlorobenzene. Then, over the course of 6 hours, 290 g of chlorine are introduced under the surface. The reaction mixture is heated to 50° C. and is then stirred until the evolution of gas ceases. A vacuum of 120 mbar is then applied and maintained for one hour. By that means there are obtained 1589 g of a solution which, according to gas chromatographic analysis, contains 30.8% of 2-chloro-5-chloromethyl-thiazole by weight. Yield: 83.2% of theory, based on 2-chloro-3-isothiocyanato-1-propene.

Distillation of 1571 g of the resulting crude solution at 75° C. and an internal pressure of 5 mbar yields 488.2 g of a material which contains 94.5% 2-chloro-5-chloromethyl-thiazole by weight.

Example P4

21 g of SO$_2$Cl$_2$ are introduced, at 20° C., into a solution of 146 g of 2-chloro-3-isothiocyanato-1-propene in 266 g of chlorobenzene. Then, at 40° C., 69 g of chlorine are introduced under the surface over the course of 5 hours. The reaction mixture is heated to 50° C. and is then stirred until the evolution of gas ceases. A vacuum of 120 mbar is then applied and maintained for one hour. There are obtained 441 g of a solution which, according to gas chromatographic analysis, contains 31.2% 2-chloro-5-chloromethyl-thiazole by weight. Yield: 81.9% of theory, based on 2-chloro-3-isothiocyanato-1-propene.

Example P5

At 20° C., 11 g of SO$_2$ and then, over the course of 6 hours, 82 g of chlorine are introduced under the surface into a solution of 146 g of 2-chloro-3-isothiocyanato-1-propene in 266 g of acetonitrile. The reaction mixture is heated to 50° C. and is then stirred until the evolution of gas ceases. A vacuum of 580 mbar is applied and maintained for one hour. By that means there are obtained 467 g of a solution which, according to gas chromatographic analysis, contains 32.7% 2-chloro-5-chloromethyl-thiazole by weight. Yield: 90.8% of theory, based on 2-chloro-3-isothiocyanato-1-propene.

Example P6

(continuous reaction procedure) At from 20° C. to 22° C., 925 g of a solution containing 33% (by weight) 2-chloro-3-isothiocyanato-1-propene in acetonitrile, 177.5 g of chlorine and 24.7 g of SO$_2$ are continuously and simultaneously introduced, per hour, into a loop reactor having a volume of 370 ml. The reaction mixture flows over into an after-reactor having an internal temperature of 50° C. Each hour there are obtained from the after-reactor 1086 g of a reaction solution containing 32.2% 2-chloro-5-chloromethyl-thiazole by weight, which corresponds to a yield of 91.1% of theory, based on 2-chloro-3-isothiocyanato-1-propene.

B) Preparation of 3-(2-chloro-thiazol-5-yl-methyl)-5-methyl-4-nitroimino-perhydro-1,3,5-oxadiazine Example P7

184 g of 3-methyl-4-nitroimino-perhydro-1,3,5-oxadiazine 100% are introduced into 400 g of dimethyl carbonate in a sulfonation flask, and 168 g of 2-chloro-5-chloromethyl-thiazole 100% are added. The mixture is heated to 65° C. While stirring at from 62 to 68° C., a mixture consisting of 350 g of dimethyl carbonate, 4 g of tetramethylammonium hydroxide pentahydrate and 242 g of potassium carbonate powder is metered in over the course of 60 minutes, thorough stirring of the reaction mixture being maintained until more than 99% of the 2-chloro-5-chloromethylthiazole has been converted.

The reaction mixture is then cooled and 600 g of water are added. The pH is adjusted to 6.5 using about 260 g of 32% hydrochloric acid; the mixture is left to stand until the phases have separated, and the organic phase is separated off. The organic phase is concentrated at 60° C. in vacuo to a final weight of 600 g. The mixture is slowly cooled to 0-5° C., which is maintained for one hour. The resulting suspension is then filtered.

218 g of the title product having a purity of from 98 to 99% (74% of theory, based on 2-chloro-5-chloromethylthiazole 100%) are obtained.

The invention relates also (B) to a process for the preparation of a compound of formula (I) as defined hereinbefore under (A), wherein c) a compound of formula (II) as defined hereinbefore under (A)

is reacted with a chlorinating agent to form a compound of formula

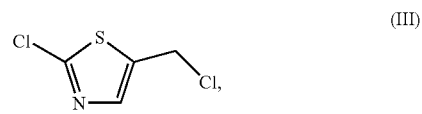

(III)

or, where appropriate, a tautomer thereof, in each case in free form or in salt form; and d) the compound of formula (III) thereby obtained is reacted with a compound of formula (IV) as defined hereinbefore under (A);

in which process the compound of formula (III) is subjected to intermediate purification in a melt crystallisation process;

to a process for the preparation of a compound of formula (III) according to process c) hereinbefore, and to the use of the compounds of formulae (II), (III) and (IV) in a process as described hereinbefore.

The compounds of formula (I) are known as valuable pesticides, and synthesis methods for those compounds are described in the literature. It has, however, been found that especially the compound of formula (III) prepared according to the processes known from the literature does not satisfy the requirements in terms of purity, that it is—probably because of those impurities—thermally unstable, which can in turn lead to significant safety problems in a production plant, and also that the known processes have significant disadvantages in respect of further parameters, for example yield and quality of the end products of formula (I) above, and the like.

The known preparation processes are therefore not satisfactory in every respect, which is why there is a need to provide improved preparation processes for the compounds of formula (I) and especially of formula (III). It has now been found that the compound of formula (III) can, using the purification process claimed according to the invention, be prepared, for example, with higher purity and that working with and storing the compound 2-chloro-5-chloromethylthiazole are associated with a significantly reduced safety risk compared to the processes known from the literature.

Purification by melt crystallisation of 2-chloro-5-chloromethylthiazole has several advantages over other purification methods. Because 2-chloro-5-chloromethylthiazole is thermally unstable and, in addition, has a "thermal memory", which means that the compound becomes more unstable with increasing thermal stress, any kind of thermal stress should be avoided as far as possible. Moreover, in the case of distillative purification, for example, it is not readily possible for all subsidiary products to be separated. Distillative purification requires columns having high numbers of plates, which requires a higher distillation temperature, combined with the correspondingly greater loss of product and reduced thermal safety of the distillation process.

Melt crystallisation normally yields at least 98% pure 2-chloro-5-chloromethylthiazole. It is also possible for the mother liquor to be recycled in order to recover the 2-chloro-5-chloromethylthiazole present therein. Melt crystallisation moreover offers the advantage that the risk of corrosion to the apparatus is minimised because of the low working temperatures and, furthermore, that neither solvents nor other additives are employed in the process.

Preference is given within the scope of the invention (B) to a process for the preparation of a compound of formula (I)

(1) wherein $R_1$ and $R_2$ in the compounds of formulae (I) and (IV) together are —$CH_2$—O—$CH_2$—, —$CH_2$—$CH_2$—$CH_2$— or —$CH_2$—$CH_2$—;

(2) wherein Q is N;

(3) wherein Y is $NO_2$;

(4) wherein Z is $NR_3$ and $R_3$ is H or $C_1$-$C_4$alkyl;

(5) wherein the purification step is carried out in process step a) at from 0° C. to +25° C., especially at from +5° C. to +15° C.;

(6) wherein X in the compound of formula (II) is halogen such as fluorine, chlorine or bromine; especially chlorine or bromine, more especially wherein X is chlorine;

(7) wherein, in process step c), there is used an aprotic polar solvent having a dielectric constant greater than 10; especially greater than 20; more especially greater than 25; very especially greater than 30;

(8) wherein, in process step c), there is used as solvent a carboxylic acid nitrile, e.g. acetonitrile, propionitrile or butyronitrile; a carboxylic acid amide, e.g. formamide, N-methylformamide, N,N-dimethylformamide, N-methylacetamide, N,N-dimethylacetamide or 1-methylpyrrolidin-2-one; a carbonic acid ester, e.g. propylene carbonate; a nitroalkane, e.g. nitromethane or nitroethane; nitrobenzene; a sulfoxide, e.g. dimethylsulfoxide; sulfolane; hexamethylphosphoric acid triamide; 1,3-dimethylimidazolidin-2-one; a urea derivative, e.g. tetramethylurea; or an ether, e.g. dioxane, tetrahydrofuran, ethylene glycol dimethyl ether or dimethoxydiethyl ether; or mixtures of such solvents;

(9) wherein as halogenating agent there is used $Cl_2$, a mixture of $Cl_2$ and $SO_2$ or a mixture of $Cl_2$ and $SO_2Cl_2$; especially wherein chlorination is performed using $Cl_2$, and $SO_2$ or $SO_2Cl_2$ is used in catalytic amounts, more especially wherein $SO_2$ or $SO_2Cl_2$ is used in an amount of from 10 to 40 mol %, based on the starting material of formula (II);

(10) wherein in process step c) a continuous procedure is employed for the preparation of the crude compound of formula (III).

The process is especially suitable for the preparation of thiamethoxam, known from WO 98/32747; and of Ti-435 (clothianidin), known from EP-A-446 913.

The dielectric constants of suitable solvents can be found, for example, in C. Reichardt, Solvents and Solvent Effects, VCH Verlagsgesellschaft, Weinheim, 1988, Table A-1, pages 408 to 410. The temperatures at which those values apply can also be found in the said table.

Otherwise, the conditions applying to process steps c) and d) are the same as those set out under invention statement (A) for process steps a) and b).

Salts of compounds of formulae (I) to (IV) can be prepared in a manner known per se as mentioned hereinbefore under invention statement (A).

Salts of compounds of formulae (I) to (IV) can also be converted into the free compounds of formulae (I) to (IV) in conventional manner as mentioned hereinbefore under invention statement (A).

Salts of compounds of formulae (I) to (IV) can be converted into different salts of compounds of formulae (I) to (IV) in a manner known per se.

The compounds of formulae (I) to (IV), and salts thereof, may also be obtained in the form of hydrates and/or may include other solvents, for example solvents that may optionally have been used for the crystallisation of compounds that occur in solid form.

The invention relates to all those embodiments of the process according to which a compound obtainable as starting material or intermediate at any stage of the process is used as starting material and all or some of the remaining steps are carried out, or in which a starting material is used in the form of a derivative or a salt and/or its racemates or antipodes, or, especially, is formed under the reaction conditions.

Compounds of formulae (I), (III) and (IV) obtainable in accordance with the process or by other means can be converted into different corresponding compounds in a manner known per se.

In the process of the present invention there are preferably used those starting materials and intermediates, in each case in free form or in salt form, which result in the compounds of formula (I) or salts thereof described at the beginning as being especially valuable.

The present invention relates also to a melt crystallisation process for purification of a compound of formula (III).

An especially preferred aspect of the invention is a continuous purification process for the compound of formula (III), for example by means of a fluid bed which has a temperature gradient.

The invention relates especially to the preparation processes described in the Examples.

The preferences applying to the substituents of compounds of formula (IV) are the same those mentioned hereinbefore in the processes for the preparation of compounds of formula (I).

The compounds of formulae (II) and (IV) are known, for example as intermediates for the preparation of pesticides, or they can be prepared using processes known per se.

PREPARATION EXAMPLES

Example P8

At 20° C., 143.2 g of sulfuryl chloride are metered into a solution of 147.5 g of 2-chloro-3-isothiocyanato-1-propene in 150 g of acetonitrile over the course of about 2 hours. The reaction is slightly exothermic. Towards the end of the reaction, the solution is heated to 40° C. and is maintained at that temperature for one hour, during which marked evolution of gas can be observed. The solvent, together with the hydrochloric acid, is concentrated in vacuo. 187.0 g of a 77% solution of 2-chloro-5-chloromethyl-thiazole are obtained, which corresponds to a yield of 86% of theory, based on 2-chloro-3-isothiocyanato-1-propene.

Example P9

At 20° C., 67.5 g of 2-chloro-3-isothiocyanato-1-propene are introduced into 75 ml of dimethylformamide, and 6.8 g of sulfuryl chloride (0.05 mol) are added to the reaction mixture. 32.5 g of chlorine are then introduced over the course of about 2 hours until an excess of starting material can no longer be detected. After the addition is complete, the reaction solution is heated to 50° C. and maintained at that temperature for one hour. Finally, the HCl formed and the solvent are drawn off in vacuo. 2-Chloro-5-chloromethyl-thiazole having a content of 72% is obtained.

Example P10

At 20° C., 87.7 g of 2-chloro-3-isothiocyanato-1-propene are introduced into 100 ml of nitromethane. 41.5 g of chlorine are then introduced over the course of about 2 hours until an excess of starting material can no longer be detected. The reaction solution is then stirred at 40° C. for one hour and is cooled again. The HCl is drawn off in vacuo and the nitromethane is distilled off. 2-Chloro-5-chloromethyl-thiazole having a content of 91% is obtained. The product contains approximately 1% of the subsidiary product of formula

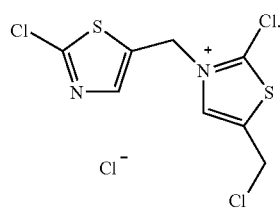

Example P11

166.6 g of 2-chloro-3-isothiocyanato-propene are introduced into 300 g of 1,2-dichloroethane in a double-walled reactor. At 30° C., 78 g of chlorine are introduced over the course of 4-5 hours. The reaction mixture is then heated to 60° C., which is maintained for 60 minutes until the evolution of gas (HCl) has ceased. The reaction mixture is then cooled to room temperature and 200 g of 37% hydrochloric acid are added, with stirring. After the phases have separated, the organic phase is extracted a further four times using 100 g of 37% hydrochloric acid each time. The aqueous extracts, which contain the product, are combined, 800 g of water are added and extraction using five portions of 1,2-dichloroethane totalling 500 g is carried out. The extracts are combined and the solvent is evaporated off. A crude melt having a content of about 92% is obtained.

Example P12

2.5 kg of liquid 2-chloro-5-chloromethyl-thiazole having a content of 95% are cooled to 10° C. in a glass beaker, provided with a seed crystal and left to stand at 10° C. for 5 hours. A two-phase mixture having a brown, liquid, upper phase and a crystalline lower phase is formed. The liquid phase is separated off and the solid phase is transferred to a filter and allowed to drain for one hour. 2.3 kg of the title product are obtained in the form of white needles having a content of more than 99% and a melting point of from 28° C. to 29° C.

Example P13

3-(2-Chloro-thiazol-5-yl-methyl)-5-methyl-4-nitroimino-perhydro-1,3,5-oxadiazine: 184 g of 3-methyl-4-nitroimino-perhydro-1,3,5-oxadiazine 100% are introduced into 400 g of dimethyl carbonate in a sulfonation flask and 170 g of 2-chloro-5-chloromethylthiazole having a content of 99% are added. The mixture is heated to 65° C. While stirring at from 62° C. to 68° C., a mixture consisting of 350 g of dimethyl carbonate, 4 g of tetramethylammonium hydroxide pentahydrate and 242 g of potassium carbonate powder are metered in over the course of 60 minutes, thorough stirring of the reaction mixture being maintained until more than 99% of the 2-chloro-5-chloromethylthiazole have been converted (monitored by LC).

The reaction mixture is then cooled and 600 g of water are added. The pH is adjusted to 6.5 using about 260 g of 32% hydrochloric acid; the mixture is left to stand until the phases have separated, and the organic phase is separated off. The organic phase is concentrated at 60° C. in vacuo to a final weight of 600 g. The mixture is slowly cooled to 0-5° C., which is maintained for one hour. The resulting suspension is then filtered.

218 g of title product having a purity of from 98 to 99% (74% of theory, based on 2-chloro-5-chloromethylthiazole 100%) are obtained.

What is claimed is:

1. A process for the preparation of a compound of formula

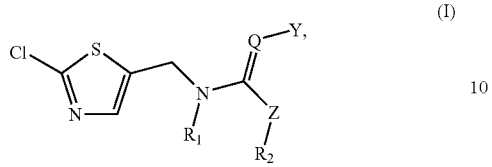

(I)

and, where appropriate, an E/Z isomer, a mixture of E/Z isomers and/or a tautomer thereof, in each case in free form or in salt form, wherein Q is CH or N;
Y is $NO_2$ or CN;
Z is $CHR_3$, O, $NR_3$ or S;
$R_1$ and $R_2$ either are each independently of the other hydrogen or $C_1$-$C_8$alkyl which is unsubstituted or substituted by $R_4$ or together are an alkylene bridge having two or three carbon atoms which optionally contains a hetero atom selected from the group consisting of $NR_5$, O and S,
$R_3$ is H or $C_1$-$C_{12}$alkyl which is unsubstituted or substituted by $R_4$,
$R_4$ is unsubstituted or substituted aryl or heteroaryl, and
$R_5$ is H or $C_1$-$C_{12}$alkyl; wherein a) a compound of formula

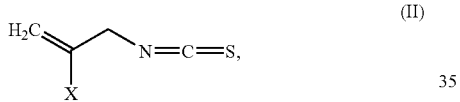

(II)

wherein X is a leaving group, is reacted with a chlorine to form a compound of formula

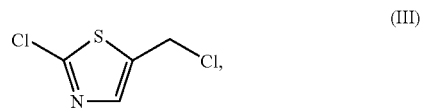

(III)

or, where appropriate, a tautomer thereof, in each case in free form or in salt form; and b) the compound of formula (III) thereby obtained is reacted with a compound of formula

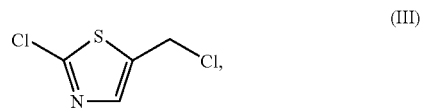

(IV)

wherein $R_1$, $R_2$, Y, Z and Q are as defined hereinbefore for the compound of formula (I);

in which process the chlorination according to process step a) is performed using chlorine in the presence of $SO_2$ in an amount of from 1 mol % to 50 mol %, based on the starting material of formula (II).

* * * * *